(12) United States Patent
Hirafuji et al.

(10) Patent No.: US 8,268,261 B2
(45) Date of Patent: Sep. 18, 2012

(54) PIPETTE CORE MEMBER, PIPETTE, AND PIPETTE DEVICE

(75) Inventors: Mamoru Hirafuji, Kanagawa (JP); Ichiro Tominaga, Kanagawa (JP); Shigeto Eda, Kanagawa (JP); Ichiro Yanagisawa, Tokyo (JP); Osamu Ohara, Chiba (JP)

(73) Assignees: Altair Corporation, Kanagawa (JP); Nano Fusion Technologies, Inc., Tokyo (JP); Kazusa DNA Research Institute, Chiba (JP)

( * ) Notice: Subject to any disclaimer, the term of this patent is extended or adjusted under 35 U.S.C. 154(b) by 221 days.

(21) Appl. No.: 12/515,846

(22) PCT Filed: Nov. 22, 2007

(86) PCT No.: PCT/JP2007/072663
§ 371 (c)(1),
(2), (4) Date: May 21, 2009

(87) PCT Pub. No.: WO2008/062869
PCT Pub. Date: May 29, 2008

(65) Prior Publication Data
US 2009/0317304 A1    Dec. 24, 2009

(30) Foreign Application Priority Data

Nov. 22, 2006 (JP) ................. 2006-316277

(51) Int. Cl.
*B01L 3/02* (2006.01)

(52) U.S. Cl. ........ 422/501; 422/509; 422/516; 422/520; 422/521; 422/522; 73/863.32; 73/864; 73/864.01; 73/864.13

(58) Field of Classification Search .............. 422/63, 422/119, 292, 515, 520, 521, 501–505, 512, 422/516, 518, 509, 522; 73/863.32, 864.01, 73/864.13, 864.23, 864.24; D24/112, 113, D24/222; 137/803, 825; 204/600
See application file for complete search history.

(56) References Cited

U.S. PATENT DOCUMENTS

| | | | | |
|---|---|---|---|---|
| 3,923,426 A | * | 12/1975 | Theeuwes | 204/630 |
| 5,304,347 A | * | 4/1994 | Mann et al. | 422/67 |
| 5,582,798 A | * | 12/1996 | Meltzer | 422/518 |
| 6,254,832 B1 | * | 7/2001 | Rainin et al. | 422/525 |

(Continued)

FOREIGN PATENT DOCUMENTS

JP        04-330270        11/1992

(Continued)

OTHER PUBLICATIONS

Q. Pu, et al. Microfabricated Electroosmotic Pump for Capillary-Based Sequential Injection Analysis. Analytica Chimica Acta (May 24, 2004); 511(1): 105-112.*

(Continued)

*Primary Examiner* — Brian R Gordon
(74) *Attorney, Agent, or Firm* — Brian R. Morrison; Westman, Champlin & Kelly, P.A.

(57) ABSTRACT

A pipette core member is used in a pipette for sampling a sample. This pipette core member includes: a pump body including a reservoir communicated with one suction/discharge port of an electroosmotic flow pump, the electroosmotic flow pump and the reservoir being integrally formed; and a capillary connected to the electroosmotic flow pump and communicated with the other suction/discharge port of the electroosmotic flow pump. The capillary is secured to the pump body.

7 Claims, 11 Drawing Sheets

U.S. PATENT DOCUMENTS

| | | | | |
|---|---|---|---|---|
| 6,296,811 | B1 * | 10/2001 | Sasaki | 422/509 |
| 6,406,605 | B1 * | 6/2002 | Moles | 204/601 |
| 6,447,661 | B1 * | 9/2002 | Chow et al. | 204/453 |
| 6,551,558 | B1 * | 4/2003 | Mann et al. | 422/518 |
| 7,077,939 | B1 * | 7/2006 | Crooks et al. | 204/450 |
| 7,231,839 | B2 * | 6/2007 | Huber et al. | 73/864.11 |
| 7,311,879 | B2 * | 12/2007 | Hodson | 422/509 |
| 7,416,706 | B2 * | 8/2008 | Brunner et al. | 422/106 |
| 7,780,830 | B2 * | 8/2010 | Haluzak et al. | 204/450 |
| 7,799,197 | B2 * | 9/2010 | Hansford et al. | 204/600 |
| 7,972,575 | B2 * | 7/2011 | Lind | 422/501 |
| 8,142,738 | B2 * | 3/2012 | Boehm et al. | 422/501 |
| 2001/0005489 | A1 * | 6/2001 | Roach et al. | 422/99 |
| 2003/0047680 | A1 | 3/2003 | Figeys et al. | |
| 2005/0034842 | A1 * | 2/2005 | Huber et al. | 165/80.4 |
| 2005/0189225 | A1 * | 9/2005 | Liu et al. | 204/600 |
| 2006/0093525 | A1 * | 5/2006 | Brunner et al. | 422/100 |
| 2006/0211133 | A1 * | 9/2006 | Corso et al. | 436/180 |
| 2007/0068815 | A1 * | 3/2007 | Lu | 204/600 |
| 2009/0308742 | A1 * | 12/2009 | Paranjape | 204/403.1 |

FOREIGN PATENT DOCUMENTS

| | | |
|---|---|---|
| JP | 11-056341 | 3/1999 |
| JP | 2004-016036 | 1/2004 |
| JP | 2005-224194 | 8/2005 |
| JP | 2005-348690 | 12/2005 |
| JP | 2006-081482 | 3/2006 |

OTHER PUBLICATIONS

International Search Report from priority Japan application No. PCT/JP2007/072663.

Form PCT/IB/338—Notification of Transmittal of Translation of the International Preliminary Report on Patentability from corresponding foreign application No. PCT/JP2007/072663, 1 page (dated Jun. 4, 2009).

Form PCT/IB/373 and PCT/ISA/237—International Preliminary Report on Patentability and Written Opinion of the International Searching Authority from corresponding foreign application No. PCT/JP2007/072663, 5 pages (dated May 26, 2009).

EPO Form 1507S—Extended European Search Report from corresponding European Application No. 07 83 2392 dated Oct. 6, 2011 (4 pages).

* cited by examiner

FIG.2(a)
FIG.2(b)
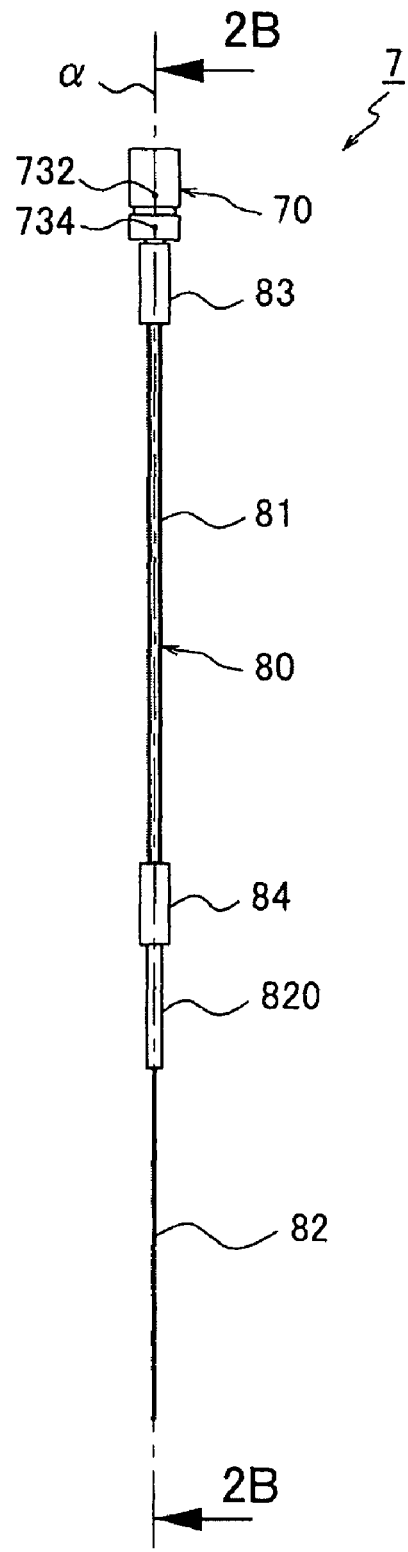
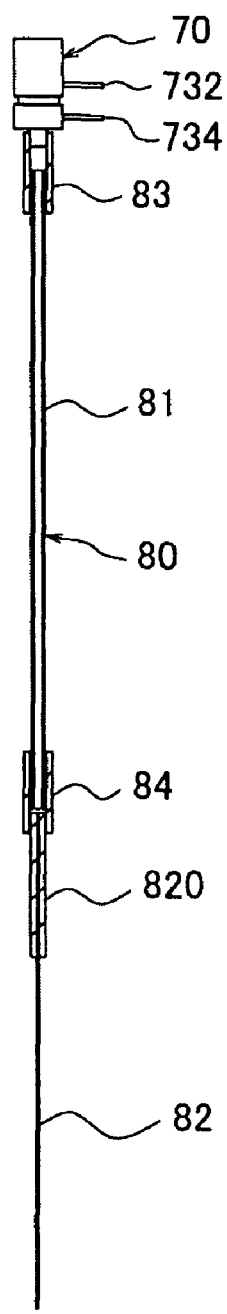

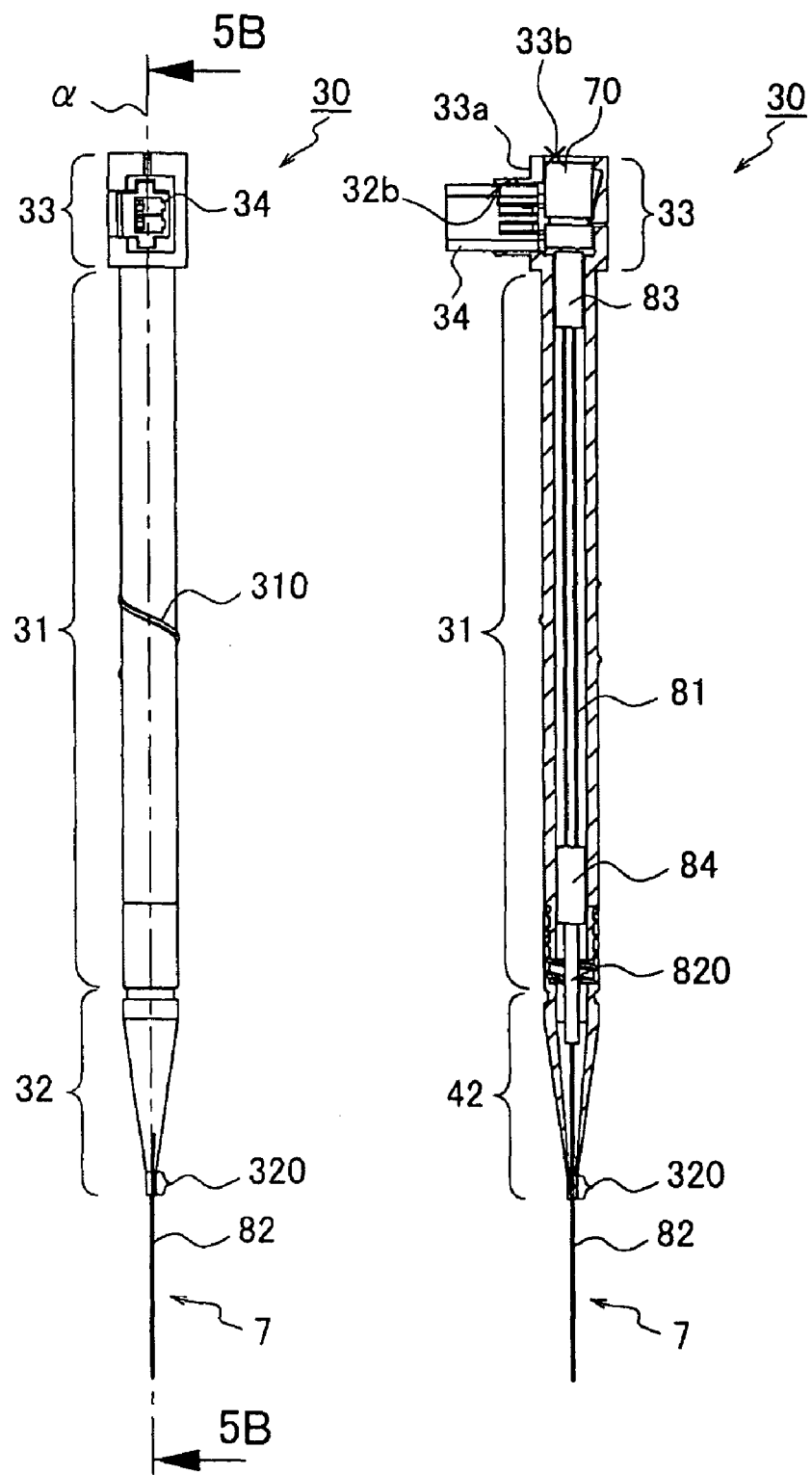

PIPETTE CORE MEMBER, PIPETTE, AND PIPETTE DEVICE

CROSS-REFERENCE TO RELATED APPLICATION

This Application is a Section 371 National Stage Application of International Application No. PCT/JP2007/072663, filed Nov. 22, 2007, and published as WO 2008/062869 on May 29, 2008, not in English.

TECHNICAL FIELD

The present invention relates to a pipette core member of a pipette for sampling a sample, such as a cell, a bacterium, fine particles, or the like, a pipette provided with the pipette core member, and a pipette device provided with the pipette.

BACKGROUND

There is a pipette for sampling an egg cell, a nucleus of the egg cell, or the like. A pipette 100 is generally operated by using a manipulator 130 as shown in FIG. 10.

The pipette 100 is attached to an attaching portion 132 extended from a fine motion unit 131 (the unit is capable of moving the attaching portion 132, to which the pipette is to be attached, horizontally and vertically at a 1 μm scale by a solenoid-operated system) of the manipulator 130. The pipette 100 is moved in any direction of x, y, and z according to a movement of the fine motion unit 131 based on instructions from the manipulator 130.

In addition, the pipette 100 includes a pump 120, and the pump 120 and the pipette 100 are connected with a tube 101.

As shown in FIG. 11, the pump 120 includes a cylinder 121 and a piston 122, and includes a stepping motor 123 for moving the piston 122 of the pump 120. The tube 101 for conveying a driving liquid is extended from the cylinder 121 of the pump 120 and a tip end of the tube 101 is connected to a longitudinal rear end of the pipette 100.

When the stepping motor 123 is rotated in accordance with instructions from the manipulator 130, a moving unit 125 connected to a driving shaft 124 of the stepping motor 123 is moved, so that the piston 122 is moved inside the cylinder 121. When the piston 122 is moved, the driving liquid inside the cylinder 121 is discharged from the cylinder 121 to the pipette 100 via the tube 101, or is sucked into the cylinder 121 from the pipette 100 via the tube 101.

With a use of the above-mentioned pipette 100, when the driving liquid is sucked by driving the pump 120 in accordance with instructions from the manipulator 130, the pipette 100 may suck a cell in a tip end of the pipette 100 or suck a sample inside the pipette 100. Conversely, when the driving liquid is discharged, the pipette 100 may discharge the sample inside the pipette 100 or discharge the cell, which has been sucked in the tip end of the pipette 100, from the tip end thereof.

There is, however, inconvenience in some operations performed by the manipulator 130.

One of the operations is transferring a plurality of cells in a Petri dish to another Petri dish.

In the case that this operation is performed by the above-mentioned manipulator 130, it is necessary to, first, place a Petri dish 140 containing cells to be transferred on a table 133, and then, move the table 133 upwardly to a position at which the cells can be manipulated by the pipette 100. After the cells are sucked into the tip end of the pipette 100 from the Petri dish 140, the table 133 is lowered. Thereafter, it is necessary to place a new Petri dish 140 on the table 133, and then, move the table 133 upwardly again to the position at which the cells can be manipulated by the pipette 100, and subsequently, discharge the cells from the tip end of the pipette 100 into the new Petri dish 140.

In view of the above, if the pipette 100 removed from the manipulator 130 can be manipulated by hand, an operation of sampling a sample by hand in conjunction with use of a microscope may be possible. Thus, there has been a demand from researchers for enabling such an operation.

In the case of the pipette 100 described above, however, every time the pipette 100 is moved, the tube 101 is largely bent and a volume of a space inside the tube 101 is changed. As a result, a suction force of the pipette 100 is changed. This change in suction force may cause discharge of the cells from the tip end of the pipette 100, or damage to the cells due to excessive suction. Consequently, it is not possible, in practice, to perform an operation of transferring cells between Petri dishes by hand.

In addition, when sampling a sample such as cells by hand using the above described pipette, a delicate manipulation and a delicate flow rate adjustment are required. However, the above described pipette 100 uses the stepping motor 123 as the pump 120, which leads to problems that a suction of a sample is performed in a stepwise manner by a certain amount, and thus, a so-called pulsating flow occurs and that a flow rate is high. If the pulsating flow occurs, excessive suction or insufficient suction of a sample may be caused, or conversely, excessive discharge or insufficient discharge of the sample may be caused. Also, if the flow rate is high, in the case of a small target sample (10 μm), it is impossible to hold the target sample in the tip end portion. Thus, it is impossible to sample a sample such as cells by hand using the pipette 100.

SUMMARY

Therefore, an object of the present invention is to provide a pipette core member used in a pipette with which an operation of sampling a sample, such as transferring cells between Petri dishes, can be performed by hand, a pipette using the pipette core member, and a pipette device provided with the pipette.

A first aspect of the present invention to achieve the above object is a pipette core member used in a pipette for sampling a sample. The pipette core member includes a pump body in which a reservoir storing a driving liquid is communicated with one suction/discharge port of an electroosmotic flow pump and the electroosmotic flow pump and the reservoir are integrally formed. The pipette core member includes a capillary connected to the electroosmotic flow pump and communicated with the other suction/discharge port of the electroosmotic flow pump. The capillary is secured to the pump body.

In the pipette core member of the present invention, since the capillary is secured to the electroosmotic flow pump, a flow path volume of the electroosmotic flow pump on a side of the capillary does not change. Accordingly, a suction force does not change, and thus, even when a pipette having the pipette core member is moved, with a cell being sucked in a tip end of the pipette core member, a discharge of the cell or a damage to the cell by excessive suction will not occur.

Also, in the pipette core member, the electroosmotic flow pump is used. The electroosmotic flow pump is capable of discharging an amount of a driving liquid proportional to a time period during which a voltage is applied, in a direction along the capillary or an opposite direction thereto. That is to say, unlike a case of a pipette using a stepping motor and a pump, a pulsating flow will not occur. In addition, control of a minute flow rate (1 μl/min or below) may be achieved. As a result, a use of a pipette with the pipette core member will not cause excessive suction or insufficient suction of a sample when sucking a sample, or conversely, cause excessive discharge or insufficient discharge of a sample.

Therefore, a use of the pipette provided with the pipette core member of the present invention makes it possible to perform an operation for sampling a sample, such as transferring a cell between Petri dishes, by hand.

Moreover, a use of the pipette core member allows an operation for sampling a sample with inexpensive equipment (a cost may be reduced to ⅕-1/10), since the manipulator explained in the Background section above is not necessary.

The capillary may be secured to the electroosmotic flow pump in any manner, as long as the flow path volume of the electroosmotic flow pump on the side of the capillary does not change. For instance, as in a second aspect of the present invention, the capillary may be secured to the electroosmotic flow pump via a tube which connects the electroosmotic flow pump and the capillary, or may be directly attached to or integrally formed with the electroosmotic flow pump.

Meanwhile, if a volume or a length of a flow path, from the other suction/discharge port of the electroosmotic flow pump to the tip end of the capillary, is too great, the suction force of the electroosmotic flow pump may not be sufficiently transmitted to the tip end of the capillary by a driving liquid and the like.

In this regard, as in a third aspect of the present invention, it is preferable that the flow path volume from the other suction/discharge port to the tip end of the capillary, opposite to a rear end which is connected to the electroosmotic flow pump, out of longitudinal ends of the capillary is 50 microliter or below.

As in a fourth aspect of the present invention, it is preferable that a length from the other suction/discharge port of the electroosmotic flow pump to the tip end of the capillary, opposite to the rear end which is connected to the electroosmotic flow pump, out of longitudinal ends of the capillary is 18 cm or below.

According to the constitution above, the suction force of the electroosmotic flow pump may be sufficiently transmitted to the tip end of the capillary.

Here, since the pipette core member of the present invention is used in the pipette which is operated by hand, the pump body is preferably small-sized and lightweighted.

Accordingly, as in a fifth aspect of the present invention, the pump body is preferably formed with a length of 20 mm or below in an alignment direction of the electroosmotic flow pump and the reservoir, and a diameter of 8 mm or below around a central axis along the alignment direction.

In addition, as in a sixth aspect of the present invention, the pump body is preferably formed with a weight of 1 g or below.

Further, as in a seventh aspect of the present invention, the pipette using the pipette core member described above preferably includes the above described pipette core member and a pipette body containing the pipette core member thereinside. The pipette body holds the pipette core member therein with the tip end of the capillary extending outward.

With a use of the pipette constituted as above, it is possible to perform an operation for sampling a sample, such as transferring a cell, by hand.

As in an eighth aspect of the present invention, it is preferable that the pipette body has a shape of a pen housing and holds the pipette core member therein with the tip end of the capillary extending outward from one end of the pipette body in an axial direction.

According to the constitution above, the pipette can be operated like a pen by hand.

Furthermore, as in a ninth aspect of the present invention, a pipette device having the above described pipette is preferably provided with a controller for controlling the electroosmotic flow pump, and a control signal line which electronically connects the electroosmotic flow pump and the controller and transmits a control signal output from the controller to the electroosmotic flow pump.

BRIEF DESCRIPTION OF THE DRAWINGS

FIG. 2 is an explanatory view of a pipette core member, in which FIG. 2(a) is a plain view of the pipette core member and FIG. 2(b) is a partial cross sectional plain view, taken from a section 2B-2B passing through a reference axis α of FIG. 2(a), of a capillary section of the pipette core member.

FIG. 3 is an explanatory view of a pump body, in which

FIG. 4 is an explanatory view of a pipette, in which

FIG. 5 is an explanatory view of a first main body of the pipette, in which FIG. 5(a) is a plain view of the first main body and FIG. 5(b) is a sectional view of the first main body taken from a section 5B-5B of FIG. 5(a).

FIG. 6 is an explanatory view of the pipette, in which

DESCRIPTION OF THE NUMERALS

1 - - - pipette device, 2 - - - pipette, 3 - - - pipette body, 7 - - - pipette core member, 9 - - - controller, 30 - - - first main body, 31 - - - body portion, 32 - - - fixing portion, 33 - - - pump housing, 33a - - - peripheral side face, 34 - - - connector holder, 40 - - - second main body, 41 - - - body portion, 42 - - - fixing portion, 70 - - - pump body, 73 - - - electroosmotic flow pump, 80 - - - capillary, 81 - - - large diameter capillary tube, 82 - - - small diameter capillary tube, 83 - - - first tube, 84 - - - connecting tube, 90 - - - controller main body, 91 - - - change-over switch, 92 - - - adjusting dial, 93 - - - connector holder, 98 - - - power supply unit, 99 - - - control signal line, 200 - - - controller, 210 - - - operation unit, 212 - - - setup button, 214 - - - voltage setting switch button, 216 - - - maximum button, 218 - - - voltage coarse adjustment dial, 220 - - - voltage fine adjustment dial, 230 - - - liquid crystal display unit, 240 - - - pump control circuit, 252 - - - CPU, 254 - - - ROM, 256 - - - RAM, 260 - - - bus, 270 - - - input and output circuit, 310 - - - screw ridge, 410 - - - thread groove, 700 - - - pump main body, 701 - - - tube portion, 701a --- other suction/discharge port, 710 --- pump portion, 711 --- pump housing space, 720 --- reservoir portion, 721 --- reservoir space, 730 --- electroosmotic material, 732 --- first electrode, 732a --- mesh electrode part, 732b --- terminal bar electrode part, 734 --- second electrode, 734a --- mesh part, 734b --- electrode terminal bar, 820 --- sleeve

DESCRIPTION

A pipette device according to an embodiment of the present invention will be described.

1. Overall Explanation of the Pipette Device

Figure 1:
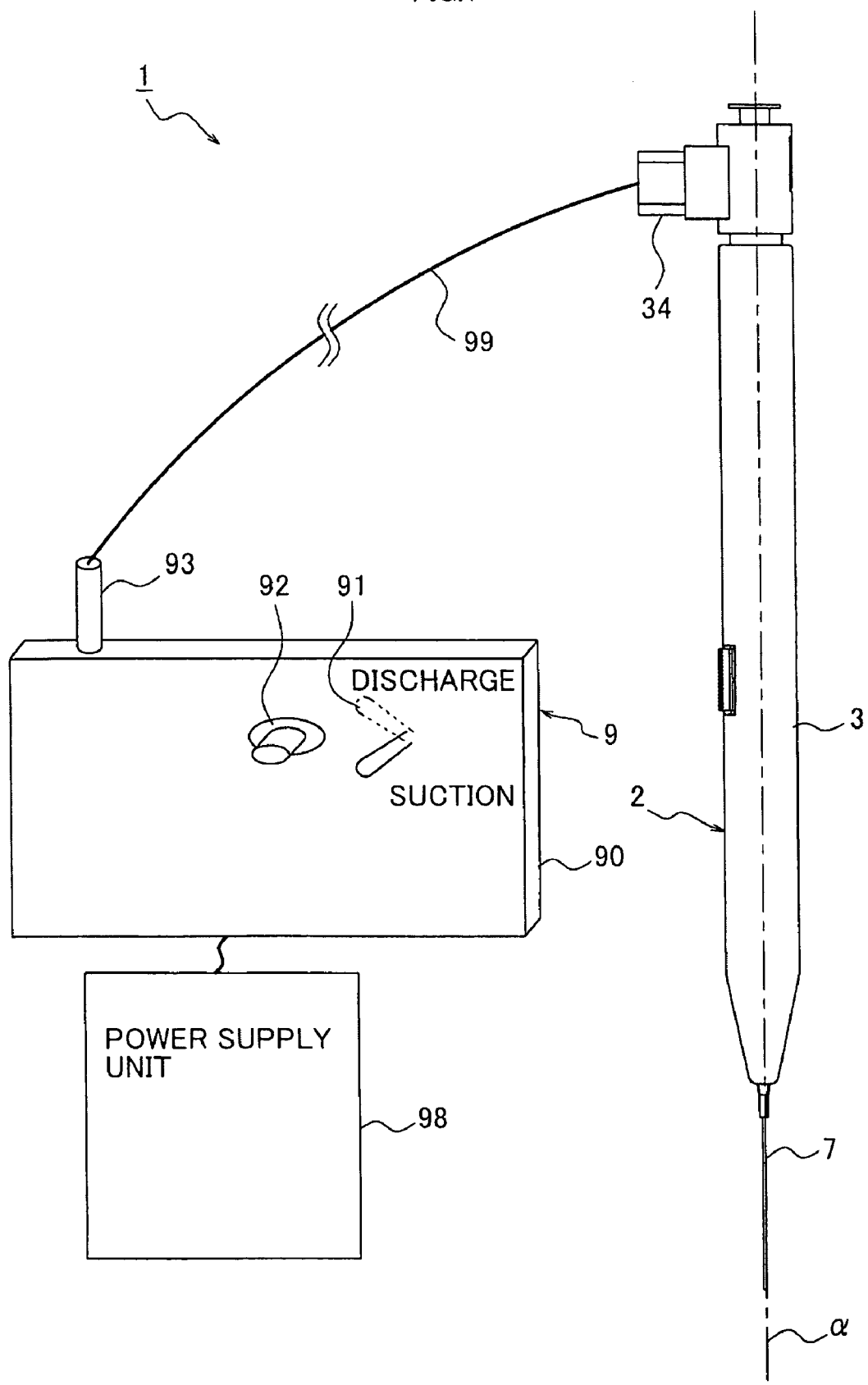
FIG. 1 is a schematic view showing a whole configuration of a pipette device 1 according to a present embodiment.

Here, FIG. 1 is a schematic view showing a whole configuration of a pipette device 1 according to a present embodiment.

The pipette device 1 of the present embodiment, as shown in FIG. 1, includes a pipette 2 and a controller 9.

The pipette 2 has a pipette body 3 formed in a substantially circular cylindrical shape like a pen housing, and has a pipette core member 7. The pipette core member 7 is contained inside the pipette body 3 in such a manner that an end of the pipette core member 7 extends outward from an axial center of one end of the pipette body 3 in an axial direction thereof along an axis of the pipette body 3. On an outer peripheral surface of the other end of the pipette body 3 in the axial direction, a connector holder 34 is erected perpendicularly to the axial direction.

The controller 9 includes a controller main body 90, a change-over switch 91 for providing instructions to the pipette 2 to switch over between suction and discharge of a sample, and a flow adjusting dial 92 for providing instructions to the pipette 2 on a suction flow amount and a discharge flow amount of the sample. A connector holder 93 is provided on a peripheral side face of the controller main body 90. The controller 9 is configured such that, when the change-over switch 91 is switched over and the adjusting dial 92 is rotated, a control signal indicating instructions corresponding to the operation of the change-over switch 91 and the adjusting dial 92 is output to outside of the controller 9 via the connector holder 93, by electric power supplied from a power supply unit 98.

The pipette 2 and the controller 9 as configured above are communicably connected to each other by inserting not shown connectors, which are provided at each end of a control signal line 99, into the respective connector holders 34 and 93.

When the buttons 91 and 92 of the controller 9 of the pipette device 1 as connected above are operated, the pipette 2 can be operated based on instructions assigned to the respective buttons 91 and 92.

In the following description, an axis which serves as a reference for defining a shape of the pipette 2 is referred to as a reference axis α. The above mentioned pipette body 3 is also formed in a substantially circular cylindrical shape having the reference axis α as its axis.

2. Pipette Core Member 7

Next, the pipette core member 7 will be explained.

Here, FIG. 2(a) and FIG. 2(b) are views illustrating a pipette core member, in which FIG. 2(a) is a plain view of the pipette core member and FIG. 2(b) is a partial cross sectional plain view, taken from a section 2B-2B passing through a reference axis a of FIG. 2(a), of a capillary portion of the pipette core member.

As shown in FIG. 2(a), the pipette core member 7 has a pump body 70 and a capillary 80.

The pump body 70 has an electroosmotic flow pump, and the capillary 80 is a thin tube having a thinness allowing handling of a cell.

Hereinafter, the pump body 70 and the capillary 80 will be each explained in more detail.

2.1. Pump Body 70

Figure 3A:
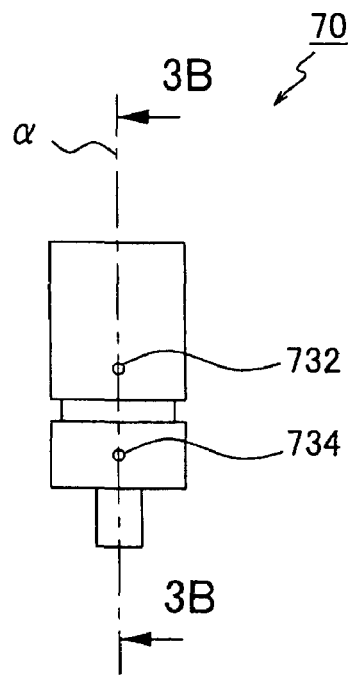
FIG. 3(a) is a plain view of the pump body and FIG. 3(b) is an enlarged sectional view of the pump body taken from a section 3B-3B passing through the reference axis α of FIG. 3(a).
Figure 3B:
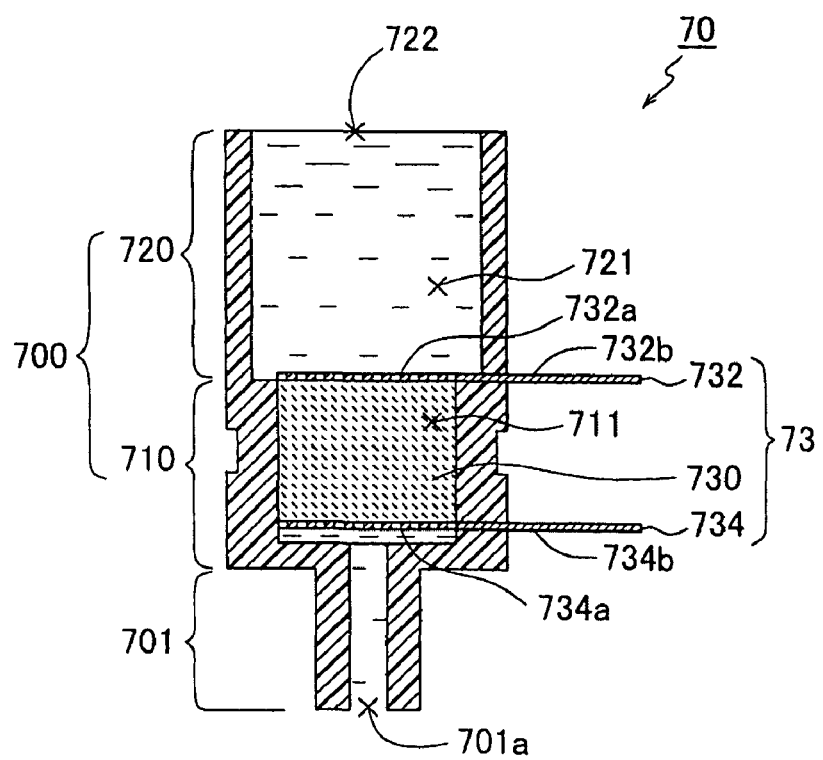

Here, FIG. 3(a) and FIG. 3(b) are explanatory views of a pump body, in which FIG. 3(a) is a plain view of the pump body and FIG. 3(b) is an enlarged sectional view of the pump body taken from a section 3B-3B passing through the reference axis α of FIG. 3(a).

As shown in FIG. 3(a), the pump body 70 is formed in a substantially circular cylindrical shape.

Also, the pump body 70 is provided with a pump main body 700 having thereinside a later-explained electroosmotic flow pump 73, and a tube portion 701 projected from the pump main body 700. The pump main body 700 and the tube portion 701 are each formed in a substantially circular cylindrical shape having the reference axis α as its axis.

Inside the pump main body 700, a pump housing space 711 is formed on a side where the tube portion 701 is provided, and a reservoir space 721 with a diameter larger than a diameter of the pump housing space 711 is formed on a side opposite to the side where the tube portion 701 is provided. Hereinafter, a portion of the pump main body 700 in which the pump housing space 711 is formed is referred to as a pump portion 710 and a portion in which the reservoir space 721 is formed is referred to as a reservoir portion 720.

The tube portion 701 is formed with a smaller diameter than a diameter of the pump main body 700 and communicates with the pump housing space 711. An inside diameter of the tube portion 701 is formed with substantially the same diameter as an outside diameter of a later-explained large diameter capillary tube 81 of the capillary 80.

A portion opposite to the pump portion 710 of the reservoir portion 720 has an opening 722, through which pure water used as a driving liquid is supplied into the reservoir space 721.

The pump body 70 configured as above is formed with a length of 18 mm in an alignment direction of the pump housing space 711 and the reservoir space 721 and with a diameter of 8 mm around a central axis along the alignment direction. Also, the pump body 70 is formed with a weight of 0.34 g.

2.1.1. Electroosmotic Flow Pump 73

As shown in FIG. 3(b), an electroosmotic flow pump 73 includes an electroosmotic material 730 and a pair of electrodes 732 and 734.

The electroosmotic material 730 is a porous body of sintered ceramics made from silica, having pore diameters ranging from several tens of nm to several μm. Also, the electroosmotic material 730 is formed into a size capable of fitting into the pump housing space 711.

The first electrode 732 is positioned at a side of the reservoir space 721 of the electroosmotic material 730 and the second electrode 734 is positioned at a side of the tube portion 701 of the electroosmotic material 730.

The first electrode 732 and the second electrode 734 include respective mesh electrode parts 732a and 734a, and respective terminal bar electrode parts 732b and 734b extended from the respective mesh electrode parts 732a and 734a.

The mesh electrode parts 732a and 734a cover whole surfaces of the electroosmotic material 730 on the reservoir space 721 side and the tube portion 701 side, respectively.

The terminal bar electrode parts 732b and 734b extend through the pump main body 700 from the mesh electrode parts 732a and 734a, and project from the outer peripheral side surface of the pump main body 700 in parallel with each other and substantially perpendicular to the reference axis α.

In the electroosmotic flow pump 73 formed as above, the driving liquid stored in the reservoir portion 720 is supplied to the electroosmotic material 730 by capillary action.

In the electroosmotic flow pump 73, when the change-over switch 91 of the controller 9 is changed over to a discharge position and the flow adjusting dial 92 is turned, the first electrode 732 is positively charged and the second electrode 734 is negatively charged. Then, the supplied driving liquid is discharged toward the tube portion 701 side.

Meanwhile, in the electroosmotic flow pump 73, when the change-over switch 91 of the controller 9 is changed over to a supply side and the flow adjusting dial 92 is turned, the first electrode 732 is negatively charged and the second electrode 734 is positively charged. Then, the driving liquid is absorbed into the electroosmotic material 730 from the tube portion 701 side.

The supply and discharge of driving liquid by the electroosmotic flow pump 73 as explained above make it possible to supply and discharge a liquid sample from a tip of the capillary 80, to suck a sample such as a cell inside the tip of the capillary 80, and to discharge the sucked sample from the inside to the outside of the capillary 80.

In the following description, a side of the mesh electrode parts 732a of the electroosmotic flow pump 73 is referred to as a suction/discharge port, and an opening 701a at a projected end of the tube portion 701 is referred to as the other suction/discharge port 701a, if necessary.

The electroosmotic flow pump 73 used here is a pump capable of sucking and discharging a driving liquid when a voltage of 3 V or less is applied to each of the first electrode 732 and the second electrode 734. The capability of the electroosmotic flow pump 73 is from several tens of pl/min to several hundreds of ml/min.

2.2. Capillary 80

Next, the capillary 80 will be explained.

The capillary 80, as shown in FIG. 2(a), is provided with the large diameter capillary tube 81, a small diameter capillary tube 82, a first tube 83, and a connecting tube 84.

The large diameter capillary tube 81 is a glass capillary tube with a diameter of 1,100 μm, and has the same diameter as the tube portion 701 of the pump body 70, as shown in FIG. 2(b).

The first tube 83 is a silicone tube having an inner space with a diameter such that the large diameter capillary tube 81 and the tube portion 701 can be inserted therein.

When the tube portion 701 of the pump body 70 and the large diameter capillary tube 81 are inserted to each side of the first tube 83, the capillary 80 is secured to the pump body 70 and is communicated with the tube portion 701.

The small diameter capillary tube 82 is a polyimide-coated glass capillary tube with a diameter of 360 μm. As shown in FIG. 2(b), a sleeve 820 for adjusting a diameter of an outer peripheral face of the small diameter capillary tube 82 to be equal to the diameter of the large diameter capillary tube 81 is attached to an end of the small diameter capillary tube 82 on the side of the large diameter capillary tube 81.

The connecting tube 84 is a silicone tube having an inner space with a diameter such that the large diameter capillary tube 81 and the small diameter capillary tube 82 on a side with the sleeve 820 can be inserted in the connecting tube 84.

When the large diameter capillary tube 81 and the small diameter capillary tube 82 are inserted to each side of the connecting tube 84, the small diameter capillary tube 82 is secured to the large diameter capillary tube 81, and the large diameter capillary tube 81 and the small diameter capillary tube 82 are communicated with each other.

In the capillary 80, a flow path is formed from the mesh electrode parts 734a to a tip end of the small diameter capillary tube 82 (an end without the sleeve 820) by connecting the large diameter capillary tube 81 and the small diameter capillary tube 82 with the second tube 84, and connecting the large diameter capillary tube 81 and the tube portion 701 with the first tube 83.

The capillary 80 in the present embodiment has a flow path volume of 7 μl, from the other suction/discharge port 701a to the tip end of the small diameter capillary tube 82.

Moreover, the capillary 80 has a length of 18 cm from the other suction/discharge port 701a of the electroosmotic flow pump 73 to the tip end of the small diameter capillary tube 82 (the end without the sleeve 820).

3. Pipette body 3

Next, the pipette body 3 will be explained.

Figure 4A:
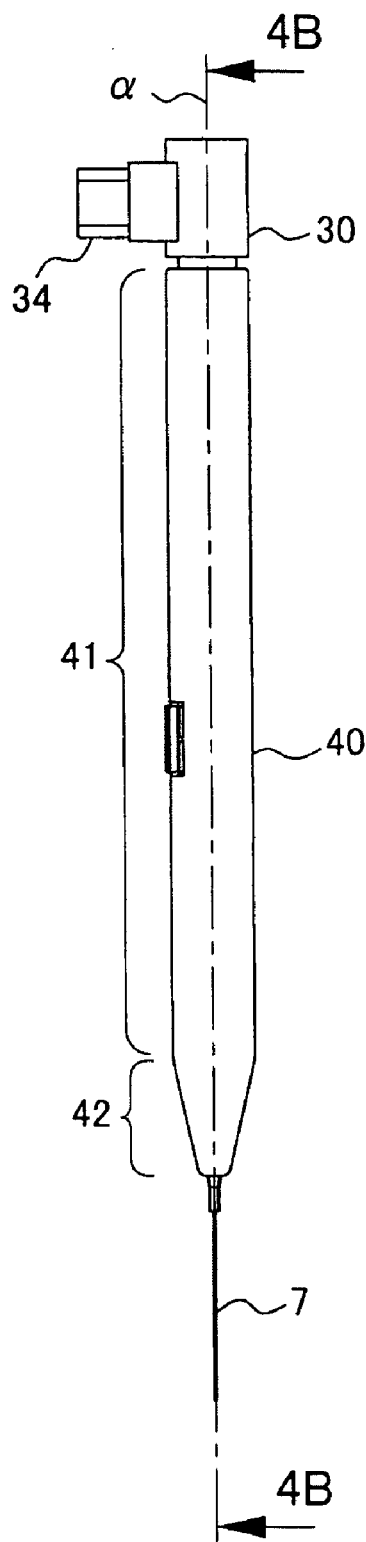
FIG. 4(a) is a plain view of the pipette and FIG. 4(b) is a sectional view of a second main body of the pipette taken from a section 4B-4B of FIG. 4(a).
Figure 4B:
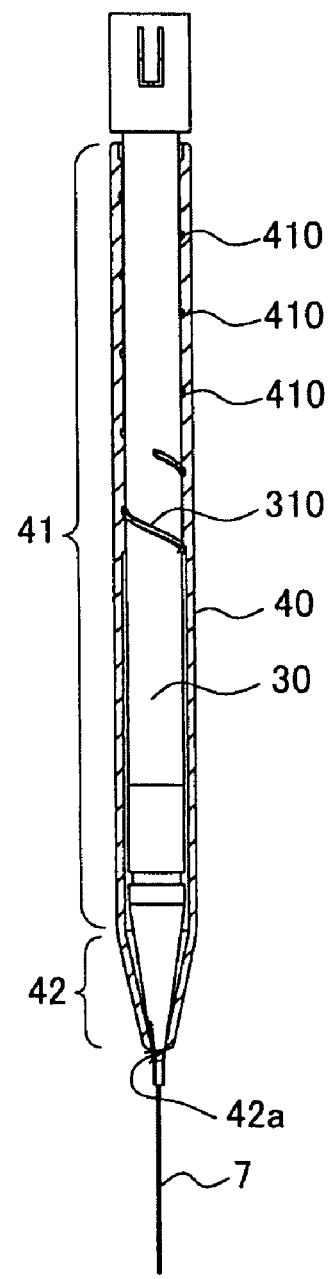
Figure 6A:
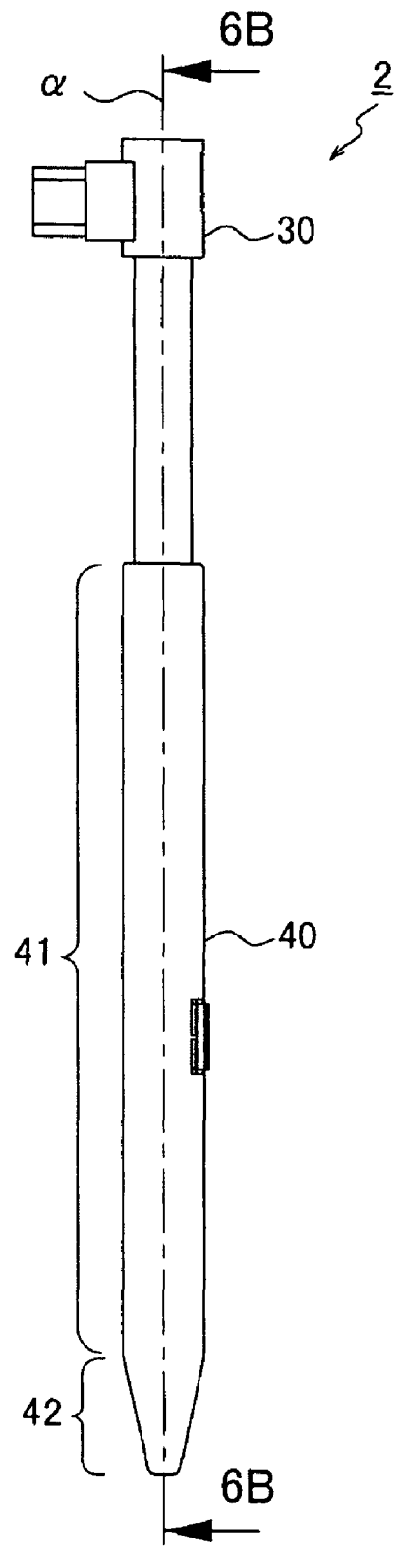
FIG. 6(a) is a plain view of the pipette and FIG. 6(b) is a sectional view of the second main body of the pipette taken from a section 6B-6B of FIG. 6(a).
Figure 6B:
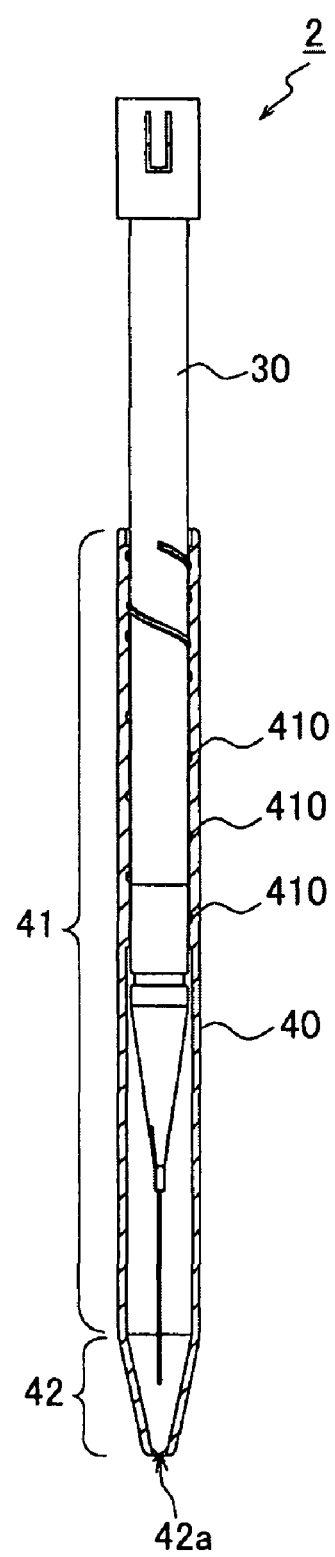

Here, FIG. 4(a) and FIG. 4(b) are explanatory views of the pipette of the present embodiment, in which FIG. 4(a) is a plain view of the pipette and FIG. 4(b) is a sectional view of a second main body of the pipette taken from a section 4B-4B of FIG. 4(a). FIG. 5(a) and FIG. 5(b) are explanatory views of a first main body of the pipette, in which FIG. 5(a) is a plain view of the first main body and FIG. 5(b) is a sectional view of the first main body taken from a section 5B-5B of FIG. 5(a). FIG. 6(a) and FIG. 6(b) are explanatory views of the pipette of the present embodiment, in which FIG. 6(a) is a plain view of the pipette and FIG. 6(b) is a sectional view of the second main body of the pipette taken from a section 6B-6B of FIG. 6(a).

As shown in FIG. 4(a), the pipette body 3 is formed in a substantially circular cylindrical shape like a pen housing.

As shown in FIG. 4(b), the pipette body 3 is provided with a first main body 30 and a second main body 40, both of which are coaxially formed about the reference axis α. The second main body 40 is formed in a size such that the first main body 30 is movable inside the second main body 40.

3.1. First Main Body 30

As shown in FIG. 5(a), the first main body 30 is formed in a substantially circular cylindrical shape having the reference axis α as its axis. In particular, the first main body 30 includes a body portion 31, a fixing portion 32, and a pump housing 33. The body portion 31 is formed in a circular cylindrical shape and is long in the axial direction. The fixing portion 32 is formed on one end side of the body portion 31 in the axial direction and has a substantially cone shape. The pump housing 33 is formed on the other end side of the body portion 31 in the axial direction and has a diameter larger than a diameter of the body portion 31.

As shown in FIG. 5(b), an inner space of the body portion 31 of the first main body 30 is formed to have an inside diameter substantially the same as outside diameters of the first tube 83 and the second tube 84 of the capillary 80 so as to allow the first tube 83 and the second tube 84 to be fittingly inserted into the inner space. Therefore, when the capillary 80 is inserted into the first main body 30, the first tube 83 and the second tube 84 of the capillary 80 are fittingly inserted into the first main body 30. Accordingly, the capillary 80 is stably held inside the first main body 30.

Moreover, the fixing portion 32 is formed in a cone shape having a bottom on a side of the body portion 31. Inside the fixing portion 32, there is formed an inner space which tapers from the bottom side toward a tip end side of the cone shape and communicates with the inner space of the body portion 31. A tip end of the fixing portion 32 is provided with a fitting insertion portion 320 having a fitting insertion hole into which the small diameter capillary tube 82 of the capillary 80 can be fittingly inserted. When the small diameter capillary tube 82 of the capillary 80 is inserted into the fitting insertion portion 320, the small diameter capillary tube 82 is stably held to the first main body 30.

The body portion 31 has a spiral thread ridge 310 formed on an outer peripheral surface thereof around the axis.

The pump housing 33 is formed with an inside diameter substantially the same as an outside diameter of the pump body 70 such that the pump body 70 is contained inside the inner space of the pump housing 33. The inner space of the pump housing 33 communicates with the inner space of the body portion 31. In addition, on a peripheral side face 33a of the pump housing 33 around the axis, there is provided an insertion hole 32b which communicates with the inner space of the pump housing 33. A connector holder 34 is inserted into the insertion hole 32b. When the connector holder 34 is inserted into the insertion hole 32b, the connector holder 34 is secured to the pump housing 33. When the connector holder 34 is inserted into the insertion hole 32b, a terminal of the connector holder 34 is connected to the terminal bar electrode parts 732b and 734b of the pump body 70 contained in the pump housing 33. As a result, when a not shown holder, provided at an end of a control signal line 99 extended from the controller 9, is inserted into the connector holder 34, the pump body 70 may be controlled by the controller 9.

The pump housing 33 is formed in a size capable of containing the pump body 70 therein. In addition, the pump housing 33 has an opening 33b in a portion, of an end face on the other end side of the first main body 30 in the axial direction, which faces the opening of the pump body 70 when the pump housing 33 contains the pump body 70. Injection of a driving liquid into the pump body 70 is performed through the opening 33b.

As explained above, when the pipette core member 7 is contained inside the first main body 30, the pipette core member 7 is held inside the first main body 30 with the tip end of the capillary 80 (the side of the small diameter capillary tube 82 without the sleeve 820) extending outward from the first main body 30.

3.2. Second Main Body 40

Next, the second main body 40 will be explained.

As shown in FIG. 4(b), the second main body 40 is formed in a substantially circular cylindrical shape having the reference axis α as its axis. In particular, the second main body 40 includes a body portion 41 and a fixing portion 42. The body portion 41 is formed in a circular cylinder shape and is long in the axial direction. The fixing portion 42 is formed on one end of the body portion 41 in the axial direction and has a substantially cone shape.

As shown in FIG. 4(b), an inner space of the body portion 41 of the second main body 40 is formed to have an inside diameter substantially the same as an outside diameter of the body portion 31 of the first main body 30 so as to allow the body portion 31 to be fittingly inserted into the inner space. Therefore, when the first main body 30 is inserted into the second main body 40, the body portion 31 of the first main body 30 is fittingly inserted inside the second main body 40. Accordingly, the first main body 30 is stably held inside the second main body 40.

Moreover, the fixing portion 42 is formed in a cone shape having a bottom on a side of the body portion 41. Inside the fixing portion 42, there is formed an inner space which tapers from the bottom side toward a tip end side of the cone shape and communicates with the inner space of the body portion 41. A tip end of the fixing portion 42 is provided with a fitting insertion hole 42a into which the tip end of the fixing portion 32, formed in a cone shape, of the first main body 30 can be fittingly inserted. When the fixing portion 32 of the first main body 30 is inserted into the fitting insertion hole 42a, the fixing portion 32 of the first main body 30 is secured, and thus, stably holds the first main body 30 to the second main body 40, in cooperation with the body portion 41.

The body portion 41 has a spiral thread groove 410 which is formed in an inner peripheral surface of the body portion 41 and engages with the thread ridge 310. A height of the thread ridge 310 and a depth of the thread groove 410 are substantially the same.

As shown in FIG. 6, the thread groove 410 is formed with a length capable of moving the first main body 30 from a position at which the tip end of the capillary 80 extending from the first main body 30 is contained within the second main body 40, to a position at which the fixing portion 32 of the first main body 30 is secured to the fixing portion 42 of the second main body 40, and thus, the tip end of the capillary 80 is exposed outside from the second main body 40, when the first main body 30 is inserted into the second main body 40 while engaging the thread ridge 310 with the thread groove 410.

When the first main body 30 is inserted in the second main body 40 as constituted above while engaging the thread ridge 310 with the thread groove 410, and then, the fixing portion 32 of the first main body 30 is inserted into the fitting insertion hole 42a of the second main body 40 to secure the first main body 30, the first main body 30 is firmly secured to the second main body 40.

Furthermore, when the first main body 30 is rotated around the axis in one direction, the first main body 30 moves within the second main body 40 while being rotated, and then the capillary 80 is contained within the second main body 40. When the first main body 30 is rotated in the other direction, the capillary 80 is exposed outside of the second main body 40.

In addition, since the height of the thread ridge 310 and the depth of the thread groove 410 are substantially the same, when the first main body 30 is inserted into the second main body 40 while engaging the thread ridge 310 with the thread groove 410, the first main body 30 is held in the second main body 40 at a position where the first main body 30 is inserted therein, unless an external force is applied.

4. Characteristic Effects of the Pipette Device of the Present Embodiment

In the pipette core member 7 used in the pipette 2 of the pipette device 1 of the present embodiment, since the capillary 80 is secured to the electroosmotic flow pump 73, a flow path volume of the electroosmotic flow pump 73 on a side of the capillary 80 does not change. Accordingly, a suction force does not change, and thus, even when the pipette 2 having the pipette core member 7 is moved, with a cell being sucked in the tip end of the pipette core member 7, a discharge of the cell or a damage to the cell by excessive suction will not occur.

Also, in the pipette core member 7, the electroosmotic flow pump 73 is used. The electroosmotic flow pump 73 is capable of discharging an amount of a driving liquid proportional to a time period during which a voltage is applied, in a direction along the capillary 80 or an opposite direction thereto. That is to say, unlike a case of a pipette using a stepping motor and a pump, a pulsating flow which interferes with a hand operation will not occur. In addition, control of a minute amount of a flow rate (1 ml/min or below) may be achieved. As a result, a use of the pipette 2 with the pipette core member 7 would not cause excessive suction or insufficient suction of a sample when sucking a sample, or conversely, cause excessive discharge or insufficient discharge of a sample.

Therefore, a use of the pipette 2 provided with the pipette core member 7 of the present embodiment makes it possible to perform an operation for sampling a sample, such as transferring a cell between Petri dishes, by hand.

Moreover, a use of the pipette core member 7 allows an operation for sampling a sample with inexpensive equipment, since the manipulator explained in the Background section above is not necessary.

Next, the capillary 80 used in the pipette 2 of the present embodiment has a flow path volume of 7 μl, from the other suction/discharge port 701*a* to the tip end of the small diameter capillary tube 82 (the end without the sleeve 820), and also to have a length of 18 cm from the opening 701*a* of the tube portion 701 to the tip end of the small diameter capillary tube 82 (the end without the sleeve 820). Accordingly, a suction force of the electroosmotic flow pump 73 may be sufficiently transmitted to the tip end of the capillary 80 by a driving liquid and the like, sampling of one cell, one bacterium, fine particles or other samples may be performed by using the pipette 2 of the present embodiment.

Further, the pump body 70 of the present embodiment has a length of 18 mm in the alignment direction of the pump housing space 711 and the reservoir space 721, and a diameter of 7 mm around a central axis along the alignment direction. Also, the pump body 70 has a weight of 0.34 g. Furthermore, in the pipette 2 of the present embodiment, the pipette body 3 has a pen shape. Since the pump body 70 is small-sized and lightweighted and the pipette body 3 has a pen shape, the pipette 2 can be smoothly operated like a pen by hand when sampling a sample such as cells.

Moreover, in the pipette 2 of the present embodiment, the first main body 30 is configured to move from a position at which the tip end of the capillary 80 is exposed outside from the second main body 40, to a position at which the tip end of the capillary 80 is contained within the second main body 40. As a result, when the pipette 2 is not in use, the tip end of the capillary 80 may be contained within the second main body 40, and thus, breakage of the capillary 80 not in use may be prevented.

Furthermore, in the pipette device 1 of the present embodiment, the pipette 2 and the controller 9 are connected with the control signal line 99. Therefore, suction and discharge with the pipette 2 may be operated, for example, by moving the pipette 2 with the right hand and manipulating the controller 9 with the left hand.

5. Other Modifications

In the above embodiment, silica is used as the electroosmotic material 730. However, oxides such as alumina, zirconia, or $TiO_2$, or polymeric materials may also be used. In the above embodiment, the electroosmotic material 730 is a porous body of sintered ceramics. However, it may be a porous body of polymeric material, or a body formed by filling and solidifying powder of fiber or the above mentioned materials (oxides such as silica, alumina, zirconia, or $TiO_2$, or polymeric materials).

In the above embodiment, the capillary 80 formed of glass is used. However, any plastics, woods, or metals, capable of forming a thin tube with an inside diameter which provides a surface tension dominant more than the gravity, may be used.

In the above embodiment, the flow path volume from the other suction/discharge port 701*a* to the tip end of the capillary 80, opposite to a rear end which is connected to the electroosmotic flow pump 73, out of longitudinal ends of the capillary 80 is 7 μl. However, the flow path volume should not be limited to the above, but should be 50 μl or less.

In the above embodiment, the length from the other suction/discharge port 701*a* to the tip end of the capillary 80, opposite to the rear end which is connected to the electroosmotic flow pump 73, out of longitudinal ends of the capillary 80 is 15.5 cm. However, the length should not be limited to the above, but should be 18 cm or less.

In the above embodiment, the length in the alignment direction of the pump housing space 711 and the reservoir space 721 is 18 mm and the diameter around the central axis along the alignment direction is 7 mm. Also, the pump body 70 is formed with a weight of 0.34 g. However, the pump body should not be limited to this configuration, but, should be formed, for example, with a length of 20 mm or less in the alignment direction of the pump housing space 711 and the reservoir space 721, and with a diameter of 10 mm or less around the central axis along the alignment direction. Also, the pump body should be formed with a weight of 1 g or less (preferably, 0.2-0.7 g).

In the above embodiment, it is configured that the controller 9 and the pipette 2 are connected by the control signal line so as to communicate by wire. However, it may be configured that the controller 9 and the pipette 2 can communicate wirelessly.

As for a driving liquid, tap water or other liquids depending on their intended use, other than pure water, may be used.

Next, a pipette device in another embodiment of the present invention will be explained.

Figure 7:
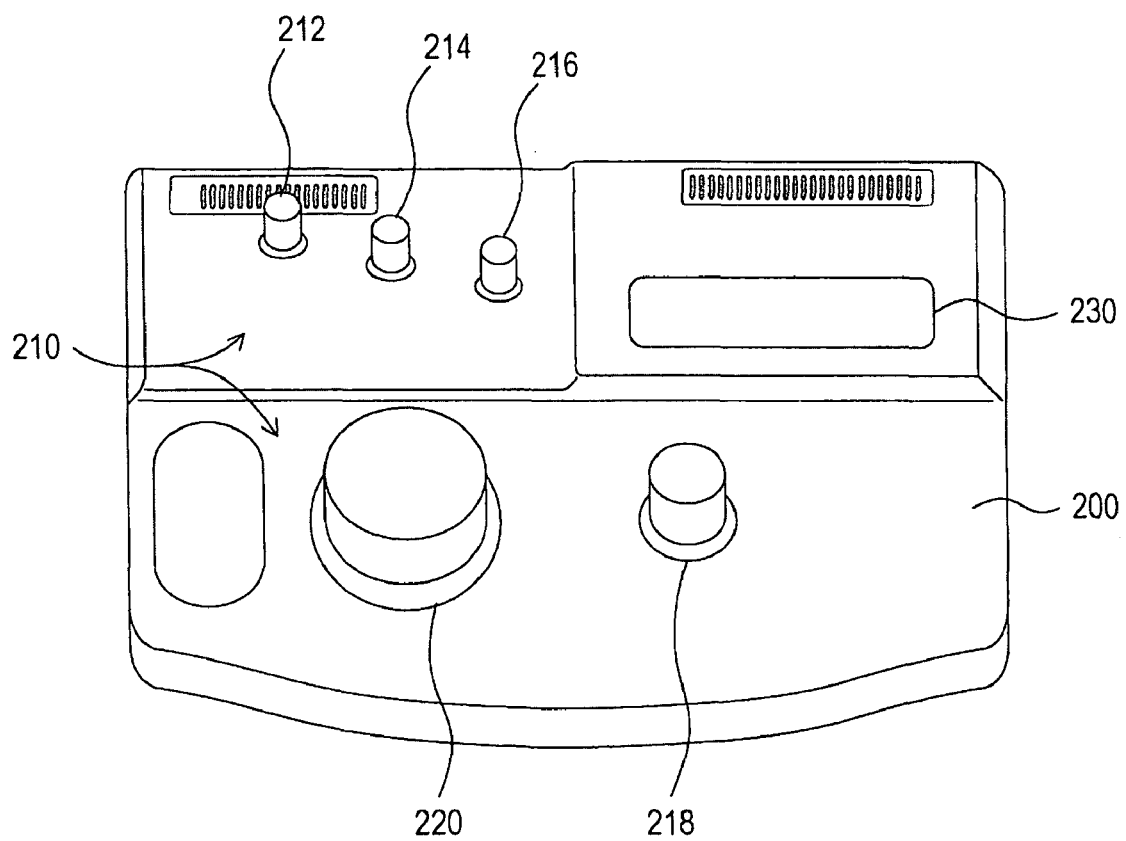
FIG. 7 is a perspective view showing an outer appearance of a console of a pipette device according to another embodiment of the present invention.

As shown in FIG. 7, a controller 200 of the pipette device of the another embodiment includes an operation unit 210 and a liquid crystal display unit 230. The operation unit 210 includes a setup button 212, a voltage setting switch button 214, a maximum button 216, a voltage coarse adjustment dial 218, and a voltage fine adjustment dial 220.

The set up button 212 is used to perform various setting operations. The voltage setting switch button 214 is used to select whether to set a voltage value at 0.1 V step or at 0.01 V step with the voltage fine adjustment dial 220. The maximum button 216 is used to instantly apply a maximum voltage to the electrodes 732 and 734 of the pump 73. The voltage coarse adjustment dial 218 is used to change a voltage at 0.5 V step, and also functions as a switch button switch between an output mode and a stop mode each time the dial is pressed. The output mode is a mode for outputting a voltage value to suck or discharge a sample. The stop mode is a mode for outputting a voltage value to retain a sample in the pipette, particularly, in a tip end of the pipette.

Now, it will be briefly explained why a predetermined voltage value is applied to retain a sample in the tip end of the pipette. In the tip end of the pipette, a suction force is always applied by capillary action. Therefore, in order to retain a sample in the tip end of the pipette, it is necessary to perform a discharge with a force equal to the suction force, and thus, a voltage for obtaining such a discharge force is applied to the electrodes.

The voltage fine adjustment dial 220 adjusts a voltage at either 0.1 V step or 0.01 V step which is set by the voltage setting switch button 214, and also functions as a switch button to switch between plus and minus of the output each time the dial is pressed. A switch-over between suction and discharge of a sample is performed by switching between plus and minus of the output.

However, since the suction force is always applied by capillary action in the tip end of the pipette as mentioned above, when a switch-over from discharge to suction is performed by switching between plus and minus with the same voltage applied, an absolute value of a suction rate becomes greater than an absolute value of a discharge rate. For the purpose of correcting this problem and of obtaining a desired suction rate or discharge rate when the output is switched over, the present embodiment allows setting of a predetermined multiplying factor (hereinafter referred to as "multiplying factor setting"), so as to output a voltage of a value multiplied by the predetermined multiplying factor. The setting is performed by pressing the set up button 212 while pressing the voltage coarse adjustment dial 218. Changing the multiplying factor is carried out by rotating the above-mentioned dial 218 and dial 220. Subsequently, when the set up button 212 is pressed, the multiplying factor which has been set is stored.

In addition, as mentioned above, setting a voltage value to retain a sample in the tip end of the pipette (hereinafter referred to as "retaining voltage setting") is performed by pressing the set up button 212 while pressing the voltage coarse adjustment dial 218, and further by pressing the voltage setting switch button 214 or the maximum button 216. Changing the voltage value to retain the sample in the tip end of the pipette is carried out by rotating the above-mentioned dial 218 and dial 220. Subsequently, when the set up button 212 is pressed, the voltage which has been set is stored.

The liquid crystal display unit 230 displays a voltage value to be set, an operating state, and the like.

Figure 8:
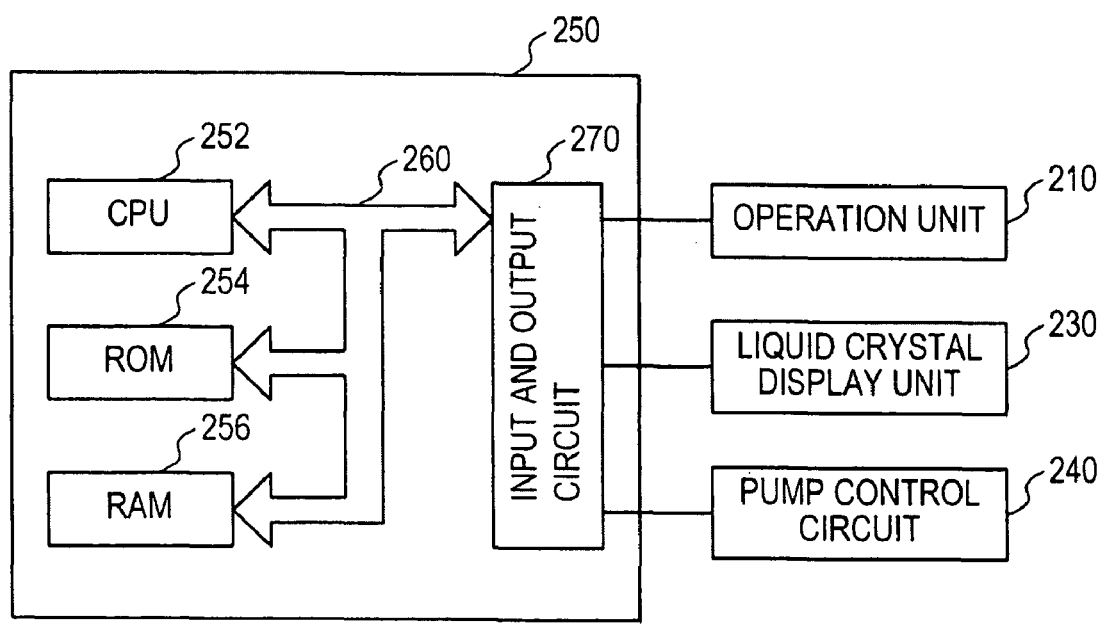
FIG. 8 is a block diagram showing an electrical configuration of the pipette device shown in FIG. 7.

As shown in FIG. 8, the pipette device includes a control unit 250 provided with a CPU 252, a ROM 254, a RAM 256, a bus 260, and an input and output circuit 270. The CPU 252 controls an overall operation of the pipette device. The ROM 254 stores an operating program of the CPU 252. The RAM 256 stores various data. The CPU 252, the ROM 254, and the RAM 256 are connected to the input and output circuit 270 via the bus 260. The input and output circuit 270 is connected to the above-mentioned operation unit 210, the liquid crystal display unit 230, and a pump control circuit 240. The pump control circuit 240 is a circuit applying a necessary voltage to the electrodes 732 and 734 of the pump 73 in accordance with instructions of the CPU 252. Since other configurations are the same as the configurations shown in FIG. 1 to FIG. 6, explanations thereof are omitted.

Figure 9:
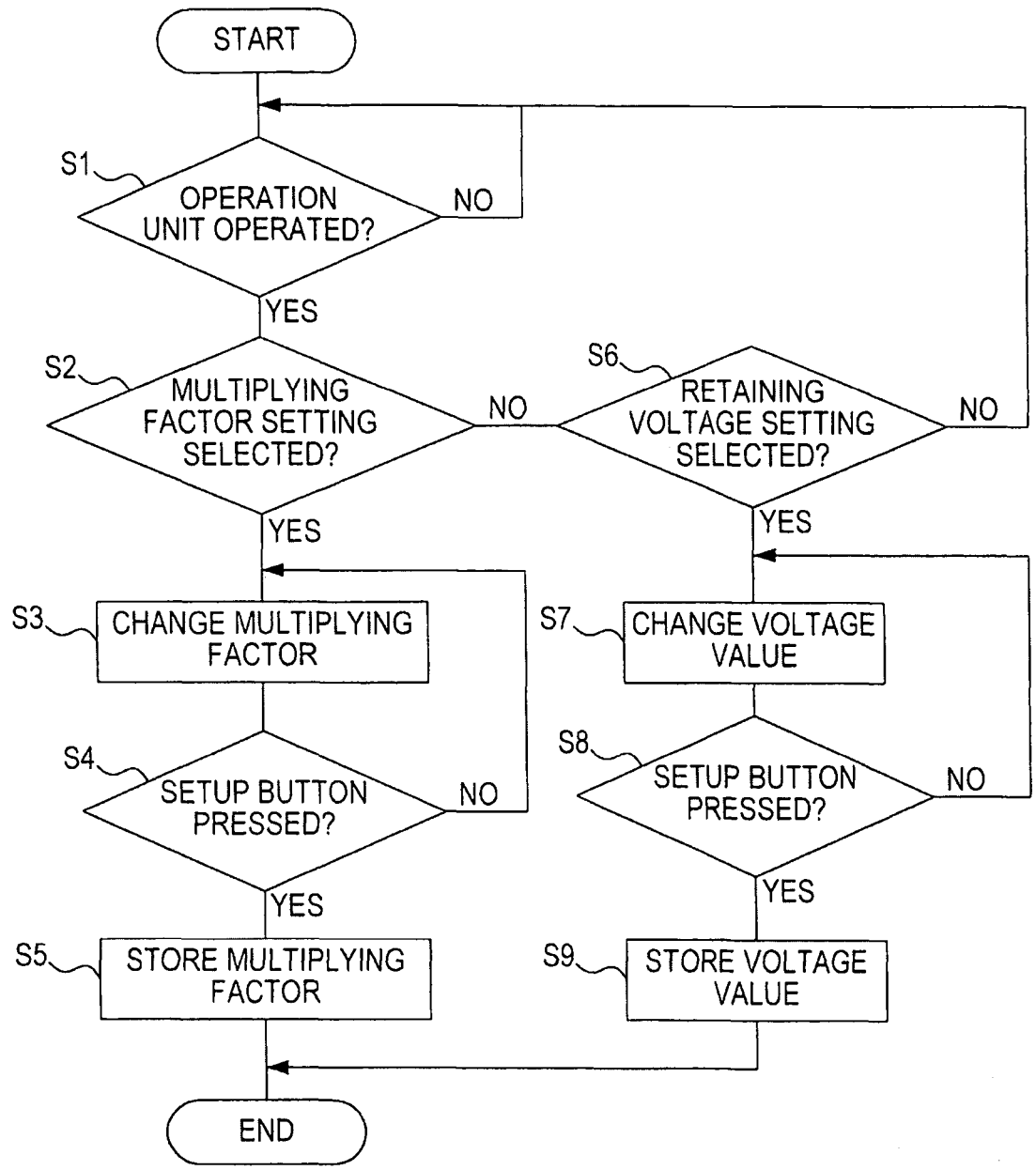
FIG. 9 is a flow diagram illustrating a magnification setting operation and a retaining voltage setting operation performed in a controller shown in FIG. 8.
Figure 10:
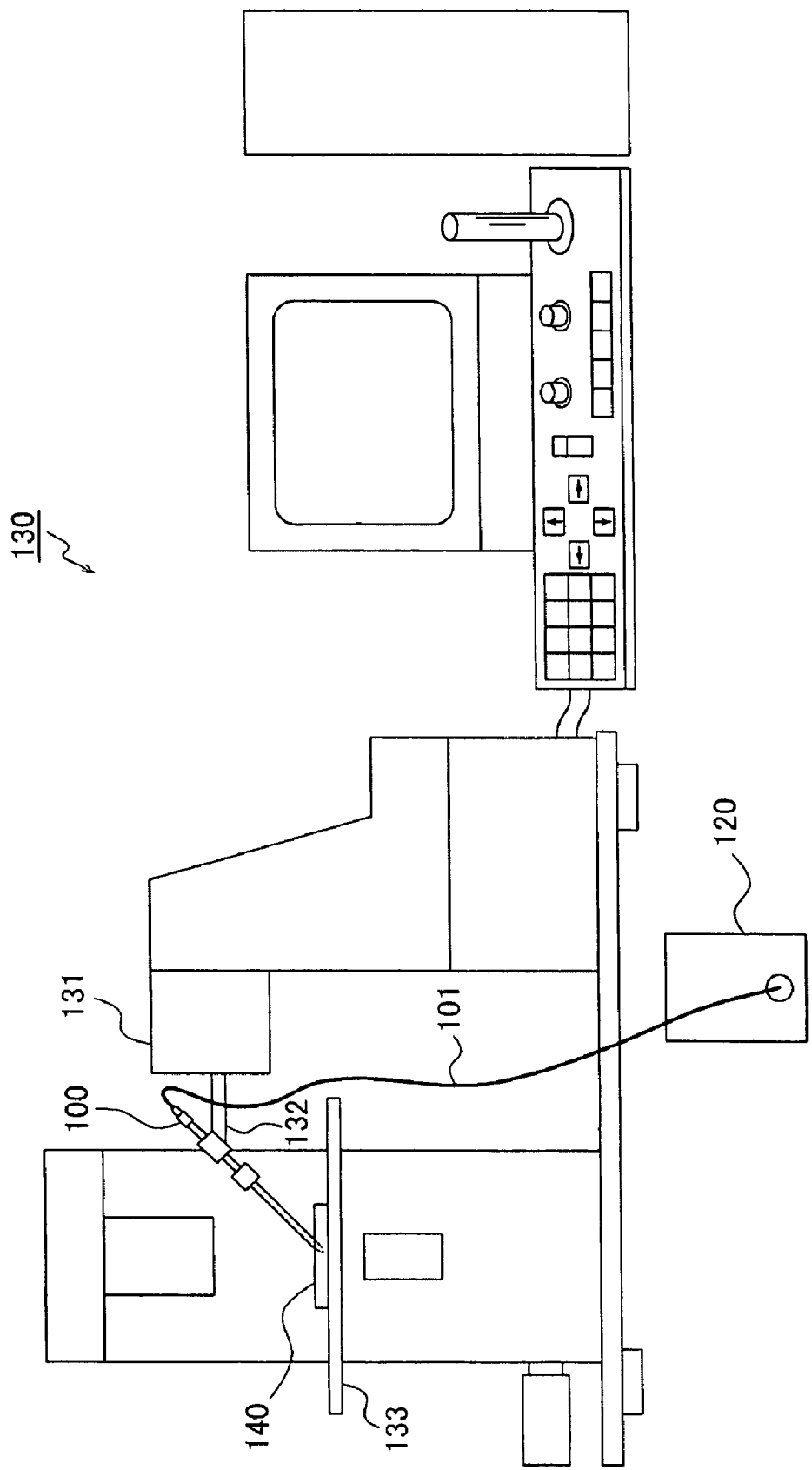
FIG. 10 is an explanatory view of a conventional pipette, which is a schematic view of a manipulator and the pipette.
Figure 11:
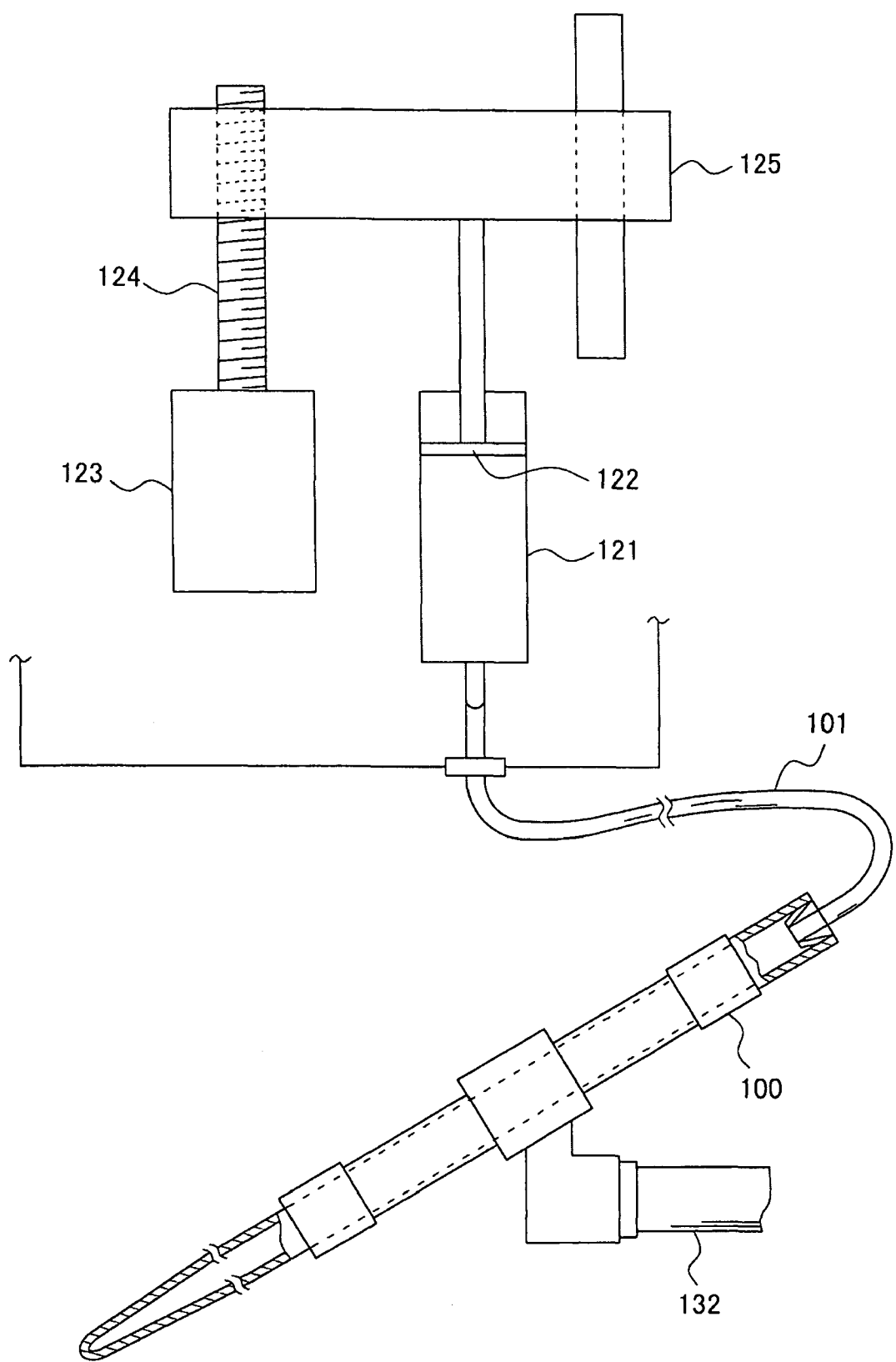
FIG. 11 is an explanatory view of the conventional pipette, which is a schematic view of the pipette and a pump.

FIG. 9 is a flow diagram illustrating a multiplying factor setting operation and a retaining voltage setting operation performed in a controller 200. Next, the multiplying factor setting operation and the retaining voltage setting operation of the pipette device of the present embodiment will be explained.

When power is turned on, the control unit 250 checks whether or not the operation unit 210 is operated (Step S1). If the operation unit 210 is not operated (Step S1: NO), the control unit 250 repeats the operation of Step 1. When the control unit 250 determines that the operation unit 210 is operated (Step S1: YES), the control unit 250 then determines whether or not a multiplying factor setting mode is selected (Step S2). As described above, if the setup button 212 is pressed while the voltage coarse adjustment dial 218 is being pressed down, the control unit 250 determines that the multiplying factor setting mode is selected.

When it is determined that the multiplying factor setting mode is selected (Step S2: YES), a multiplying factor can be changed. An operator of the pipette device can change the multiplying factor by rotating the dial 218 and the dial 220. If the multiplying factor is changed by the dials 218 and 220, the changed value is displayed on the liquid crystal display unit 230 (Step S3). Next, the control unit 250 determines whether or not the setup button 212 is pressed (Step S4). If the setup button 212 is not pressed (Step S4: NO), the present process returns to Step S3 so that the multiplying factor can be changed. If the setup button 212 is pressed (Step S4: YES), a magnification which has been set is stored at a predetermined area of the RAM 256 (Step S5).

On the other hand, when it is determined in Step 2 that the magnification setting mode is not selected (Step S2: NO), the present process proceeds to Step S6 and it is determined whether or not retaining voltage setting is selected. When it is determined that the retaining voltage setting is selected (Step S6: YES), the retaining voltage can be changed. The operator of the pipette device can change the retaining voltage by rotating the dial 218 and the dial 220. If the voltage is changed by the dials 218 and 220, the changed value is displayed on the liquid crystal display unit 230 (Step S7). Next, the control unit 250 determines whether or not the setup button 212 is pressed (Step S8). If the setup button 212 is not pressed (Step S8: NO), the present process returns to Step S7 so that the retaining voltage can be changed. If the setup button 212 is pressed (Step S8: YES), then, a voltage value which has been set is stored at a predetermined area of the RAM 256 (Step S9). If a negative determination is made in Step S6, the present process returns to Step S1.

Once the multiplying factor setting mode or the retaining voltage setting mode is selected, information on the selected mode is stored at a predetermined area of the RAM 256. Then, if it is determined that the setup button 212 is once again pressed in Step S1, it is then determined in Step S2 or Step S6 which of the multiplying factor setting mode and the stored voltage setting mode is selected, the multiplying factor or the voltage is changed in Step S3 or S7, and a changed multiplying factor or a changed voltage is stored in Step S9.

Thus, in order to set a voltage for instantly retaining a minute object at a desired position while manipulating the minute object under microscopic observation using the pipette device, when the setup button 212 is pressed, a voltage at that time is stored, and the stored value is updated each time the setup button 212 is pressed.

As above, the present embodiment makes it possible to easily perform sucking or discharging a sample at a desired suction rate or discharge rate with the pipette, and retaining a sample in the tip end of the pipette.

A tip end of a pipette as a disposable item is subject to frequent replacement, and thus, a suction force may change depending on a diameter and a length of the tip end of the pipette. Therefore, a retaining voltage needs to be set in accordance with such changes. Additionally, the pipette device of the present embodiment has an excellent operability since retaining voltage setting may be easily performed.

The invention claimed is:

1. A pipette device comprising:
   a pipette comprising:
      a pipette body; and
      a pipette core member retained inside the pipette body, the pipette core member comprising:
         a pump body comprising:
            an electroosmotic flow pump having a first suction/discharge port and a second suction/discharge port, wherein the electroosmotic flow pump further comprises a first electrode, a second electrode, and an electroosmotic material sandwiched between the first electrode and the second electrode; and
            a reservoir integrally formed with the electroosmotic flow pump, and configured to store a driving liquid and in liquid communication with the first suction/discharge port of the electroosmotic flow pump; and
         a capillary secured to the pump body and connected to the electroosmotic flow pump, wherein the capillary also communicates with the second suction/discharge port of the electroosmotic flow pump;

a controller having a setting device that sets a voltage value of a control signal output that is used for retaining a sample in a tip end of the capillary of the pipette, wherein the setting device comprises:

a switch device that switches polarity of the voltage value of the control signal output applied to the electroosmotic flow pump; and a multiplying factor setting device configured to multiply the voltage value by a predetermined multiplying factor; and a control signal line that electronically connects the electroosmotic flow pump and the controller and transmits the control signal output from the controller to the electroosmotic flow pump.

2. The pipette device according to claim 1, wherein the capillary is connected to the electroosmotic flow pump via a tube connecting the electroosmotic flow pump and the capillary.

3. The pipette device according to claim 1, wherein a flow path volume from the second suction/discharge port to a tip end of the capillary is 50 microliters or below.

4. The pipette device according to claim 1, wherein a length from the second suction/discharge port to the tip end of the capillary is 18 centimeters or below.

5. The pipette device according to claim 1, wherein the pump body is formed with a length of 20 millimeters or below in an alignment direction of the electroosmotic flow pump and the reservoir, and a diameter of 8 millimeters or below around a central axis along the alignment direction.

6. The pipette device according to claim 1, wherein the pump body is formed with a weight of 1 gram or below.

7. The pipette device according to claim 1, wherein the pipette body has a cylindrical housing with a tapered end, and holds the pipette core member therein with the tip end of the capillary extending outward from the tapered end of the pipette body in an axial direction of the cylindrical housing.

* * * * *